(12) United States Patent
Waldhoff et al.

(10) Patent No.: US 8,449,476 B2
(45) Date of Patent: May 28, 2013

(54) MULTIPLE CONFIGURATION ELECTRONIC THERMOMETER

(75) Inventors: Gary J. Waldhoff, Maryland Heights, MO (US); Michael E. Bisch, Kirkwood, MO (US); Denis Y. Yerlikaya, Des Peres, MO (US)

(73) Assignee: Covidien LP, Mansfield, MA (US)

( * ) Notice: Subject to any disclaimer, the term of this patent is extended or adjusted under 35 U.S.C. 154(b) by 193 days.

(21) Appl. No.: 12/796,920

(22) Filed: Jun. 9, 2010

(65) Prior Publication Data

US 2010/0250909 A1    Sep. 30, 2010

Related U.S. Application Data

(62) Division of application No. 11/752,155, filed on May 22, 2007, now Pat. No. 7,749,170.

(51) Int. Cl.
*A61B 5/00* (2006.01)
*G01F 1/08* (2006.01)
*G01K 1/14* (2006.01)
*G01K 13/00* (2006.01)
*G01K 1/00* (2006.01)

(52) U.S. Cl.
USPC ........... 600/549; 600/300; 374/141; 374/163; 374/208

(58) Field of Classification Search
USPC ................. 374/141, 163, 208; 600/300, 549
See application file for complete search history.

(56) References Cited

U.S. PATENT DOCUMENTS

| | | | |
|---|---|---|---|
| 3,702,076 A | 11/1972 | Georgi | |
| 3,729,998 A | 5/1973 | Mueller et al. | |
| 3,893,058 A | 7/1975 | Keith | |
| 3,915,003 A | 10/1975 | Adams | |
| 4,008,614 A | 2/1977 | Turner et al. | |
| 4,054,057 A | 10/1977 | Kluge | |
| 4,112,762 A | 9/1978 | Turner et al. | |
| 4,143,348 A | 3/1979 | Hoge | |
| 4,161,880 A | 7/1979 | Prosky | |
| 4,183,248 A | 1/1980 | West | |
| 4,282,507 A | 8/1981 | Tindall et al. | |

(Continued)

FOREIGN PATENT DOCUMENTS

| | | |
|---|---|---|
| DE | 102008022615 A1 | 11/2009 |
| EP | 1039281 A1 | 9/2000 |

(Continued)

OTHER PUBLICATIONS

Office action dated Apr. 14, 2008 from U.S. Appl. No. 11/752,155, 13 pages.

(Continued)

*Primary Examiner* — Sean Dougherty
(74) *Attorney, Agent, or Firm* — Lisa E. Winsor, Esq.

(57) ABSTRACT

A plurality of custom thermometer models are manufactured from a universal clinical thermometer core. The thermometer core includes a housing, a controller storing a software program, a power source, a probe, a probe cord, and a display. A plurality of model selection devices are produced, each corresponding to a different thermometer model. One of the model selection devices is selected and connected to the controller. The controller operates the thermometer as a function of the connected model selection device such that the thermometer is configured with the features and default settings of the thermometer model corresponding to the connected model selection device.

14 Claims, 10 Drawing Sheets

U.S. PATENT DOCUMENTS

| | | | |
|---|---|---|---|
| 4,307,373 A | 12/1981 | Johnston | |
| 4,317,367 A | 3/1982 | Schonberger | |
| 4,411,535 A | 10/1983 | Schwarzschild | |
| 4,420,738 A | 12/1983 | Rehmann et al. | |
| 4,437,084 A | 3/1984 | Clayton, Jr. | |
| 4,447,884 A | 5/1984 | Wada | |
| 4,464,067 A | 8/1984 | Hanaoka | |
| 4,487,208 A | 12/1984 | Kamens | |
| 4,531,842 A | 7/1985 | Schonberger | |
| 4,536,851 A | 8/1985 | Germanton et al. | |
| 4,572,365 A | 2/1986 | Bruno et al. | |
| 4,574,359 A | 3/1986 | Ishizaka et al. | |
| 4,592,000 A | 5/1986 | Ishizaka et al. | |
| 4,602,871 A | 7/1986 | Hanaoka | |
| 4,629,336 A | 12/1986 | Ishizaka | |
| 4,642,785 A | 2/1987 | Packard et al. | |
| 4,727,500 A | 2/1988 | Jackson et al. | |
| 4,728,199 A | 3/1988 | Murai et al. | |
| 4,729,672 A | 3/1988 | Takagi | |
| 4,733,974 A | 3/1988 | Hagerman | |
| 4,735,512 A | 4/1988 | Suzuki | |
| 4,762,429 A | 8/1988 | Fujikawa | |
| 4,771,791 A | 9/1988 | Kubouchi | |
| 4,811,198 A | 3/1989 | Ota et al. | |
| 4,843,577 A | 6/1989 | Muramoto | |
| 4,866,621 A | 9/1989 | Ono | |
| 4,878,184 A | 10/1989 | Okada et al. | |
| D309,866 S | 8/1990 | Fukuda et al. | |
| 4,986,669 A | 1/1991 | Yamaguchi | |
| 5,013,161 A | 5/1991 | Zaragoza et al. | |
| 5,037,488 A | 8/1991 | Wienand | |
| 5,066,141 A | 11/1991 | Ikeda et al. | |
| 5,088,837 A | 2/1992 | Shiokawa et al. | |
| 5,116,136 A | 5/1992 | Newman et al. | |
| 5,142,266 A | 8/1992 | Friese et al. | |
| 5,165,798 A | 11/1992 | Watanabe | |
| 5,207,765 A | 5/1993 | Eiermann et al. | |
| 5,259,389 A | 11/1993 | Muramoto et al. | |
| 5,305,381 A | 4/1994 | Wang et al. | |
| 5,307,263 A | 4/1994 | Brown | |
| 5,370,459 A | 12/1994 | Culbertson et al. | |
| 5,388,134 A | 2/1995 | Douglass et al. | |
| 5,392,031 A | 2/1995 | Toriumi et al. | |
| 5,417,207 A | 5/1995 | Young et al. | |
| 5,438,322 A | 8/1995 | Martin et al. | |
| 5,445,154 A | 8/1995 | Larson et al. | |
| 5,458,121 A | 10/1995 | Harada | |
| 5,473,629 A | 12/1995 | Muramoto | |
| 5,473,937 A | 12/1995 | McCluskey et al. | |
| 5,497,139 A | 3/1996 | Takahashi et al. | |
| 5,575,563 A | 11/1996 | Chiu et al. | |
| 5,632,555 A | 5/1997 | Gregory et al. | |
| 5,700,416 A | 12/1997 | Masui et al. | |
| 5,725,308 A | 3/1998 | Smith et al. | |
| 5,738,441 A | 4/1998 | Cambridge et al. | |
| 5,749,656 A | 5/1998 | Boehm et al. | |
| D395,609 S | 6/1998 | Knieriem et al. | |
| 5,789,920 A | 8/1998 | Gass | |
| 5,820,263 A | 10/1998 | Ciobanu | |
| 5,883,646 A | 3/1999 | Beauchamp | |
| 5,887,338 A | 3/1999 | Wildgen | |
| 5,961,451 A | 10/1999 | Reber et al. | |
| 6,006,120 A | 12/1999 | Levin | |
| 6,068,399 A | 5/2000 | Tseng | |
| 6,091,317 A | 7/2000 | Lyle et al. | |
| 6,147,335 A | 11/2000 | Von Arx et al. | |
| 6,236,880 B1 | 5/2001 | Raylman et al. | |
| 6,241,146 B1 | 6/2001 | Wienand et al. | |
| 6,280,397 B1 | 8/2001 | Yarden et al. | |
| 6,286,995 B1 | 9/2001 | Takahashi et al. | |
| 6,293,700 B1 | 9/2001 | Lund et al. | |
| 6,297,723 B1 | 10/2001 | Shoji et al. | |
| 6,319,448 B1 | 11/2001 | Kirchdoerffer et al. | |
| 6,383,144 B1 | 5/2002 | Mooney et al. | |
| 6,418,359 B1 | 7/2002 | Wolf et al. | |
| 6,494,830 B1 | 12/2002 | Wessel | |
| 6,511,478 B1 | 1/2003 | Burnside et al. | |
| 6,534,994 B1 | 3/2003 | Doderer et al. | |
| 6,558,320 B1* | 5/2003 | Causey et al. | 600/300 |
| 6,568,849 B1 | 5/2003 | Chen et al. | |
| 6,588,931 B2 | 7/2003 | Betzner et al. | |
| 6,591,703 B2 | 7/2003 | Gass et al. | |
| 6,607,302 B2 | 8/2003 | Lyle | |
| 6,634,789 B2* | 10/2003 | Babkes | 374/208 |
| 6,637,935 B2 | 10/2003 | Chen | |
| 6,639,505 B2 | 10/2003 | Murata et al. | |
| 6,686,828 B2 | 2/2004 | Bernitz et al. | |
| 6,698,922 B2 | 3/2004 | Adachi et al. | |
| 6,699,188 B2 | 3/2004 | Wessel | |
| 6,730,025 B1 | 5/2004 | Platt | |
| 6,746,150 B2 | 6/2004 | Wienand et al. | |
| 6,756,585 B2 | 6/2004 | Damaschke | |
| 6,782,744 B1 | 8/2004 | Tashiro et al. | |
| 6,789,936 B1 | 9/2004 | Kraus et al. | |
| 6,827,487 B2 | 12/2004 | Baumbach | |
| 6,827,488 B2 | 12/2004 | Knieriem et al. | |
| 6,836,651 B2 | 12/2004 | Segal et al. | |
| 6,839,651 B2 | 1/2005 | Lantz et al. | |
| 6,854,880 B2 | 2/2005 | Hsieh | |
| 6,880,969 B2 | 4/2005 | Adachi et al. | |
| 6,899,457 B2 | 5/2005 | Kurano | |
| 6,918,696 B2 | 7/2005 | Hoshisashi et al. | |
| 6,938,474 B2 | 9/2005 | Melvas | |
| 6,939,039 B2 | 9/2005 | Brunvoll | |
| 6,957,911 B2* | 10/2005 | Wong et al. | 374/208 |
| 6,969,354 B1 | 11/2005 | Marian | |
| 6,976,783 B2 | 12/2005 | Chen | |
| 6,981,796 B2 | 1/2006 | Hsieh | |
| 7,004,622 B2 | 2/2006 | Hardwicke et al. | |
| 7,021,824 B2 | 4/2006 | Wawro et al. | |
| 7,028,568 B2 | 4/2006 | Tokunaga et al. | |
| 7,036,984 B2 | 5/2006 | Penney et al. | |
| 7,115,850 B2 | 10/2006 | Niemann et al. | |
| 7,183,779 B2 | 2/2007 | Hughes | |
| 7,198,402 B2 | 4/2007 | Ruettiger | |
| 7,218,129 B2 | 5/2007 | Beaman et al. | |
| 7,219,544 B2 | 5/2007 | Tanaka et al. | |
| 7,255,475 B2* | 8/2007 | Quinn et al. | 374/163 |
| 7,267,547 B2 | 9/2007 | Schmid et al. | |
| 7,303,332 B2 | 12/2007 | Yu | |
| 7,314,310 B2 | 1/2008 | Medero | |
| 7,316,507 B2* | 1/2008 | Sisk et al. | 374/208 |
| 7,374,336 B2 | 5/2008 | Fraden | |
| 7,395,173 B2 | 7/2008 | Kautz et al. | |
| 7,434,991 B2 | 10/2008 | Harr et al. | |
| 7,507,021 B2* | 3/2009 | Yerlikaya et al. | 374/142 |
| 7,549,792 B2 | 6/2009 | Bisch et al. | |
| 7,613,590 B2 | 11/2009 | Brown | |
| 7,654,735 B2* | 2/2010 | Sisk et al. | 374/100 |
| 7,722,247 B2 | 5/2010 | Yerlikaya | |
| 7,959,579 B2* | 6/2011 | Dijkman | 600/561 |
| 7,976,475 B2* | 7/2011 | Dijkman | 600/561 |
| 2002/0002326 A1* | 1/2002 | Causey et al. | 600/300 |
| 2002/0090020 A1 | 7/2002 | Yu | |
| 2002/0109577 A1 | 8/2002 | Loose et al. | |
| 2002/0135454 A1 | 9/2002 | Ichida et al. | |
| 2002/0181545 A1* | 12/2002 | Babkes | 374/208 |
| 2003/0002562 A1 | 1/2003 | Yerlikaya et al. | |
| 2003/0149349 A1 | 8/2003 | Jensen | |
| 2003/0176810 A1 | 9/2003 | Maahs et al. | |
| 2003/0212438 A1* | 11/2003 | Nova et al. | 607/30 |
| 2004/0071182 A1* | 4/2004 | Quinn et al. | 374/1 |
| 2004/0081225 A1 | 4/2004 | Janicek | |
| 2004/0264546 A1* | 12/2004 | Wong et al. | 374/209 |
| 2005/0187415 A1 | 8/2005 | Azizkhan et al. | |
| 2005/0249263 A1* | 11/2005 | Yerlikaya et al. | 374/209 |
| 2006/0061451 A1 | 3/2006 | Chen | |
| 2007/0189358 A1* | 8/2007 | Lane et al. | 374/121 |
| 2008/0294065 A1 | 11/2008 | Waldhoff et al. | |
| 2009/0118618 A1 | 5/2009 | Harhen | |
| 2010/0006327 A1 | 1/2010 | Yu et al. | |

FOREIGN PATENT DOCUMENTS

| | | |
|---|---|---|
| EP | 1569352 A2 | 8/2005 |
| FR | 2580806 A1 | 10/1986 |
| GB | 2266771 A | 11/1993 |
| GB | 2284566 A | 6/1995 |

| | | | |
|---|---|---|---|
| JP | 01312432 A | 12/1989 |
| JP | 02049129 A | 2/1990 |
| JP | 6241914 A | 9/1994 |
| JP | 0989680 A | 4/1997 |
| JP | 11030553 A | 2/1999 |
| JP | 11-173922 A | 7/1999 |
| JP | 2006186357 A | 7/2006 |
| WO | 0131305 A1 | 5/2001 |
| WO | 03001994 A1 | 1/2003 |
| WO | 03002966 A1 | 1/2003 |
| WO | 03103174 A1 | 12/2003 |
| WO | 2004107989 A1 | 12/2004 |
| WO | 2008115237 A1 | 9/2008 |

OTHER PUBLICATIONS

Response filed Jul. 14, 2008 to Office action issued Apr. 14, 2008 in U.S. Appl. No. 11/752,155, 8 pages.
Office action dated Sep. 17, 2008 from U.S. Appl. No. 11/752,155, 11 pages.
Response filed Dec. 2, 2008 to Office action issued Sep. 17, 2008 in U.S. Appl. No. 11/752,155, 9 pages.
Office action dated Feb. 6, 2009 from U.S. Appl. No. 11/752,155, 10 pages.
Response filed Jun. 29, 2009 to Office action issued Feb. 6, 2009 in U.S. Appl. No. 11/752,155, 8 pages.
Office action dated Oct. 13, 2009 from U.S. Appl. No. 11/752,155, 12 pages.
Response filed Dec. 11, 2009 to Office action issued Oct. 13, 2009 in U.S. Appl. No. 11/752,155, 9 pages.
European Search Report regarding related application serial No. EP 08156626.7 dated Feb. 2, 2011, 6 pages.

* cited by examiner

MULTIPLE CONFIGURATION ELECTRONIC THERMOMETER

CROSS-REFERENCE TO RELATED APPLICATION

The present application is a divisional of U.S. application Ser. No. 11/752,155, filed May 22, 2007.

BACKGROUND

Although clinical thermometers often share similar traits, a single model cannot meet the different needs of all, or even most, users. For example, a user in an emergency room setting may desire a relatively simple electronic thermometer for quickly and easily obtaining a temperature measurement for a patient. With simplicity in mind, the user interface is designed such that the user can turn on the thermometer, take a temperature reading, and then turn it off. On the other hand, in a pediatric office setting, for example, a user may desire additional functions such as the ability to switch between one predictive mode and another or between a predictive mode and a direct measurement mode, or the ability to switch between different patient body locations (e.g., rectal, oral, or in an axilla) for taking temperature measurements. In addition, users in different countries often have different expectations for performance, functionality, and the like. Thus, a manufacturer must produce several different models of a thermometer, which may have the same basic parts (i.e., a housing, a controller, a probe, and a display), but have different user interfaces, menus, software features, and the like.

SUMMARY

Aspects of the invention relate to a method of manufacturing a universal electronic thermometer that is automatically configured, upon initialization, as a particular thermometer model of a plurality of thermometer models. Each thermometer, even when functioning as a different model, includes the same housing, the same embedded software, and the same controller assembly. A user input device is selected from a plurality of user input devices. Each of the user input devices is associated with an operating configuration of the medical device. The selected user input device is connected to a controller of the medical device. The controller has a memory storing one or more computer-executable instructions for implementing a plurality of functions of the medical device. The controller is configured for operating the medical device in a selected operating configuration as a function of the selected user input device connected thereto. The configured controller executes software instructions selected from the one or more software instructions to implement one or more of the plurality of functions of the medical device upon configuring.

A system for manufacturing configured medical devices embodying aspects of the invention includes a plurality of non-configured medical devices, each of which has a controller associated therewith for implementing a plurality of functions. The system includes a plurality of interchangeable model selection devices for configuring the medical devices according to a plurality of pre-defined operating configurations. At least one of the configurations is defined by a set of one or more of the functions of the medical devices and at least one of the configurations is defined by another set of one or more of the functions of the medical devices. A selected one of the model selection devices is connected to the controller of each of the medical devices. The controller is responsive to the selected model selection device connected thereto for configuring the associated medical device to operate in the configuration corresponding to the selected model selection device.

In another aspect, a method of manufacturing a custom thermometer includes selecting a user input device from a plurality of user input devices. Each of the user input devices is associated with an operating configuration of a configurable thermometer. The selected user input device is connected to a controller of the configurable thermometer. The controller has a memory storing one or more computer-executable instructions for implementing a plurality of functions of the configurable thermometer. The controller is configured for operating the configurable thermometer in a selected operating configuration as a custom thermometer. The configured controller is operable in the selected operating configuration to implement one or more of the plurality of functions of the configurable thermometer as a function of the selected user input device connected thereto.

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Other features will be in part apparent and in part pointed out hereinafter.

BRIEF DESCRIPTION OF THE DRAWINGS

Corresponding reference characters indicate corresponding parts throughout the drawings.

DETAILED DESCRIPTION

Figure 1:
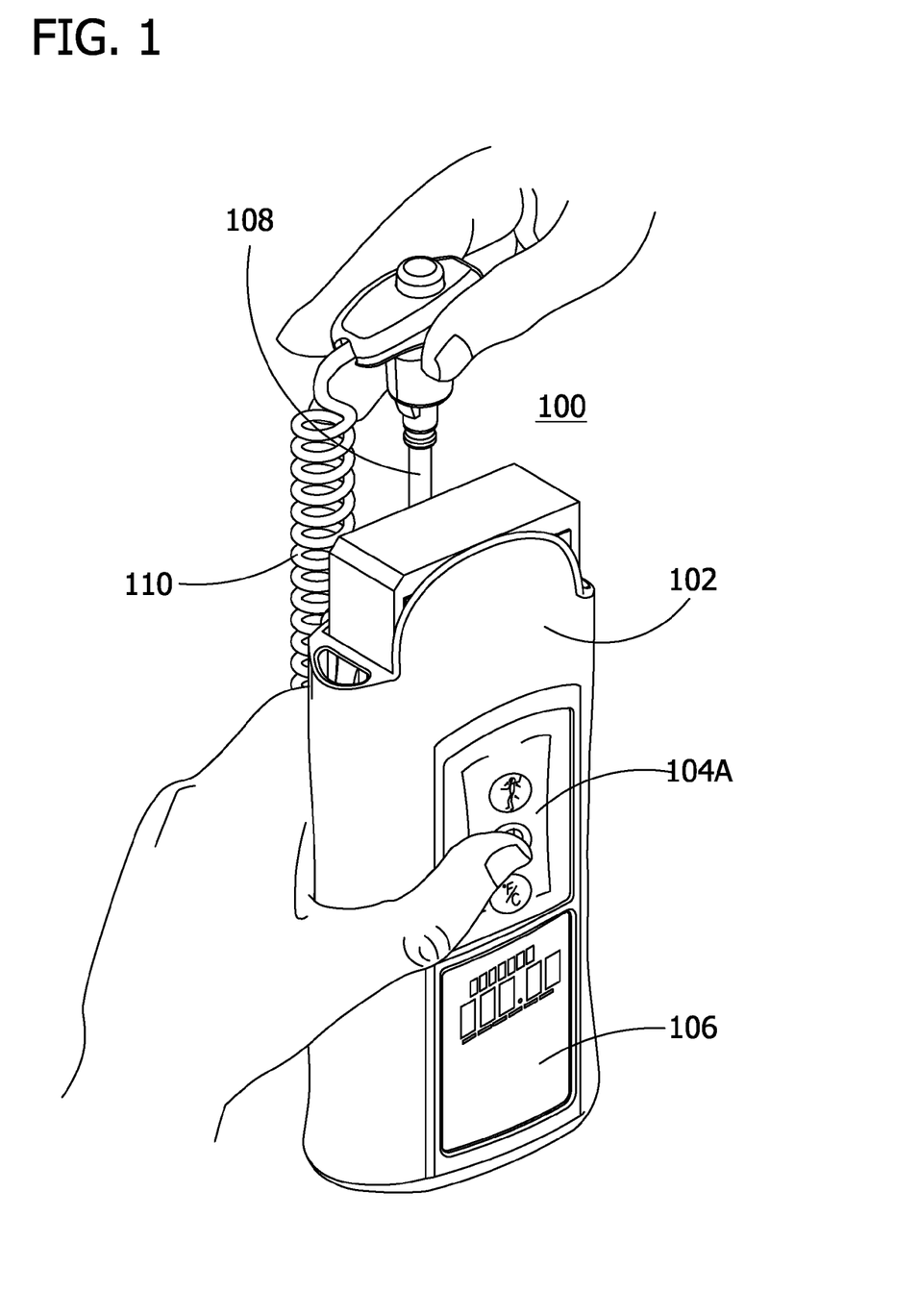
FIG. 1 is a perspective of an electronic thermometer according to an embodiment of the invention.
Figure 2:
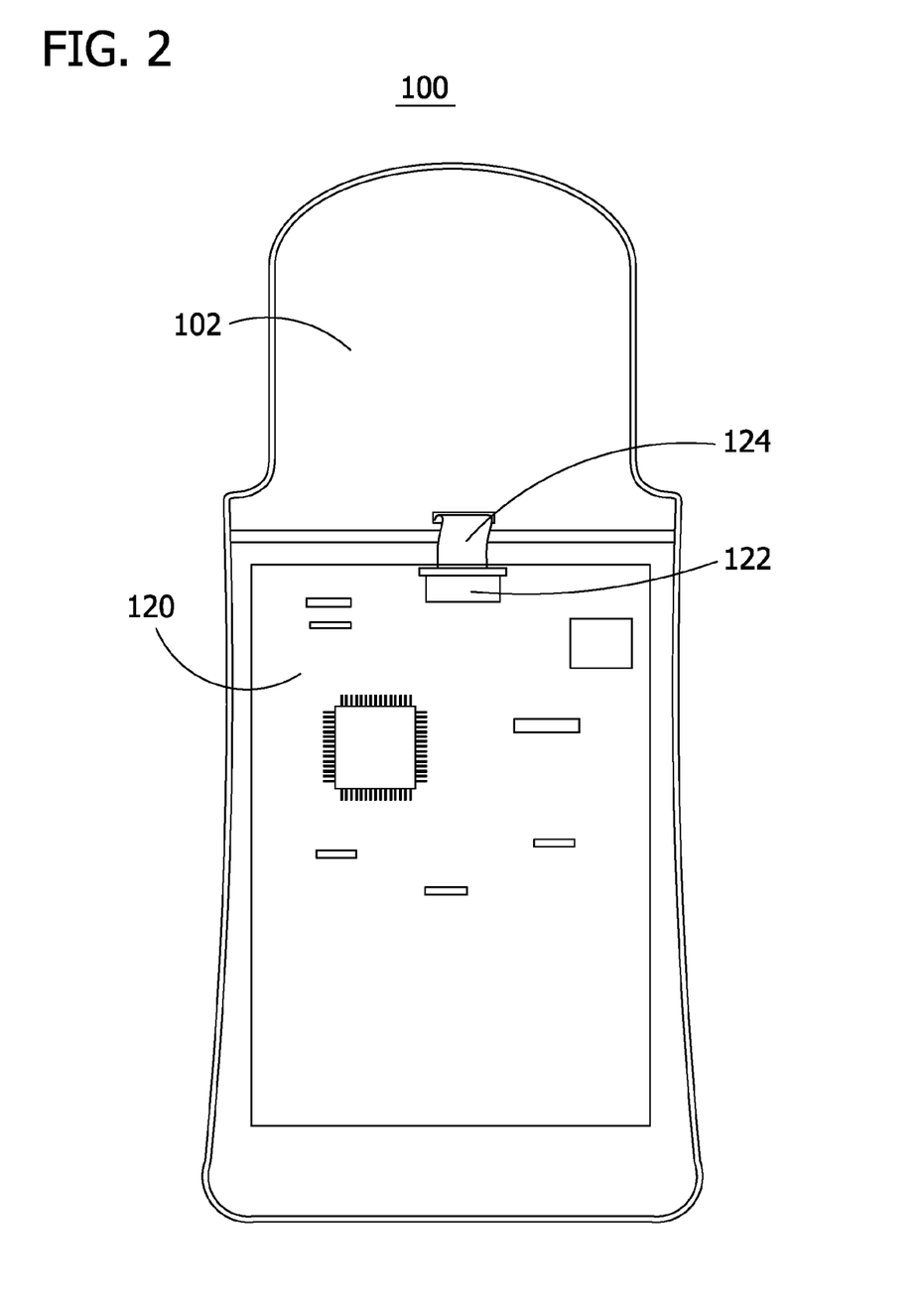
FIG. 2 is a back view of the thermometer of FIG. 1 having a model selection device installed and a portion of the housing removed.

Referring to FIGS. 1 and 2, FIG. 1 shows a side elevation view of a clinical thermometer, generally indicated at 100, according to one embodiment, and FIG. 2 shows a perspective view of the back of the thermometer 100 with a portion of a housing 102 of the thermometer 100 removed. The thermometer 100 includes the housing 102, a user input device such as keypad 104A, a display 106, a controller 120, a power supply (e.g. a battery), and a probe 108, which is attached to the housing 102 and controller 120 via a probe cord 110. The controller 120 includes a user input device connector 122 for connecting to the keypad 104A, and a software program having computer executable instructions for displaying the menus of and performing the functions of the thermometer 100. The keypad 104A also includes a cable 124 for connecting to the user input device connector 122 of the controller 120.

In the illustrated embodiment, the user input device connector 122 shown is a pin header having a plurality of pins for engaging an appropriate pin header connector. But other types of mating electrical connectors, such as spade terminals and connectors or soldered connections are within the scope of the invention. The cable 124 may be a ribbon cable, a collection of individual wires, or some other conductive means for establishing a connection between the keypad 104A and the controller 120. It is also contemplated that the user input device 104A may directly engage the user input device connector 122, may be directly installed on the circuit board of the controller 120, or may communicate with the controller 120 through a wireless means such as Radio Frequency Identification, all of which eliminate cable 124.

According to aspects of the invention, thermometer 100 constitutes a universal electronic thermometer that is automatically configured, upon initialization, as a particular thermometer model of a plurality of thermometer models. The thermometer 100, even when functioning as a different model, may include the same housing 102 and the same controller 120. The controller 120 of universal thermometer 100 has a memory (see FIG. 6) storing a software program containing instructions for implementing all of the user interface menus and features of which the thermometer is capable. A model selection device (e.g., a user input device such as keypad 104A) corresponding to one particular thermometer model is selected from a plurality of such devices and connected to controller 120 as described above. Depending on which model selection device is connected, controller 120 enables and/or disables functions in the software program. It is contemplated that the model selection device may also be a sticker for identifying the thermometer model, a model identification nameplate, or the like, each including means for connecting to controller 120.

Figure 3:
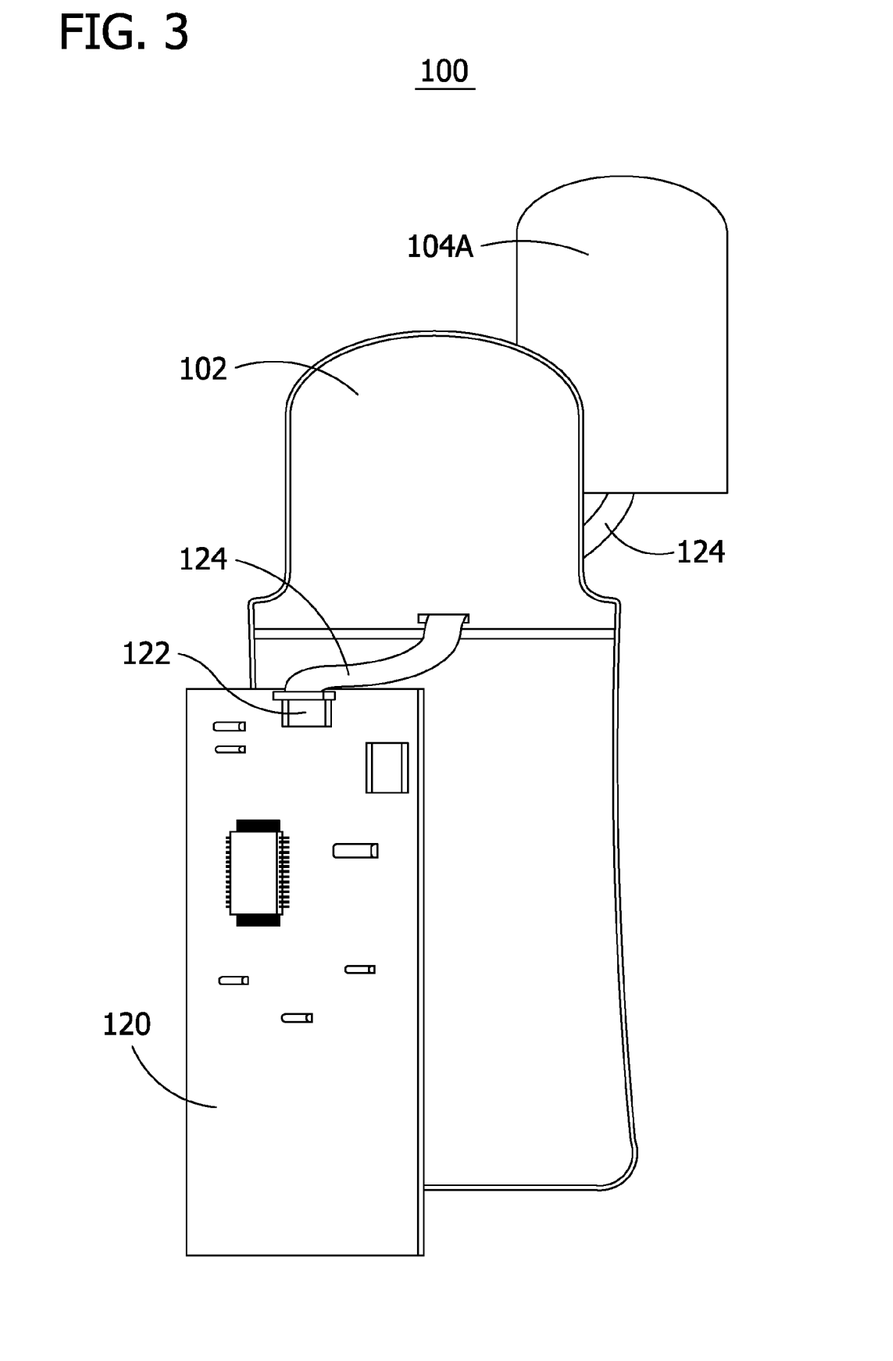
FIG. 3 is a partially exploded back view of the thermometer of FIG. 2.

Referring to FIG. 3, the thermometer 100 is shown from the side, partially exploded. The cable 124 on keypad 104A fits through a hole in the housing 102 to engage the connector 122 of the controller 120. Thus, when the thermometer 100 is fully assembled, the controller 120 is fitted within the rear of housing 102, and the keypad 104A is affixed to the front of housing 102, adjacent to the display 106 as shown in FIG. 1.

In operation according to an embodiment of the invention, a user causes the thermometer 100 to initialize by removing probe 108 from its stored position, the user places the probe 108 in contact with a patient at the appropriate temperature measurement location (e.g., oral, rectal, or in an axilla), and the probe 108 passes temperature information to the controller 120 via the probe cord 110. The controller 120 determines the patient's temperature and displays the determined patient temperature to the user via the display 106. All models of clinical thermometers generally perform this measurement function, but different thermometer models have different default settings, features, and user interface configurations (e.g., menus). For example, one model is manufactured with a fast predictive mode for use when temperature measurement speed is more important than accuracy as the default mode of operation and provides a slower, user-selectable standard predictive mode for use when accuracy is more important than speed, such as disclosed in commonly assigned U.S. patent application Ser. No. 11/539,438, filed Oct. 6, 2006, the entire disclosure of which is incorporated herein by reference. Conversely, another model is manufactured with the standard predictive mode as the default mode and the fast predictive mode as a user-selectable option. Some models may not allow the thermometer to operate in a measurement mode other than the default mode such that menus related to switching between the fast and standard predictive mode may be eliminated from these models. Some models may also allow a user to manually adjust or calibrate the thermometer, while others do not. Other features and options that are enabled or have default settings determined by the model of the thermometer include: direct measurement mode (no prediction algorithms used to speed up measurements), anti-theft settings, preheat temperature, programmable device identification number, sound themes, backlight, measurement counter, LCD display test screens, and battery voltage readout. Regardless of the default settings, features, and user interface configuration, all of the thermometer models have the same basic parts as described above.

Figure 4A:
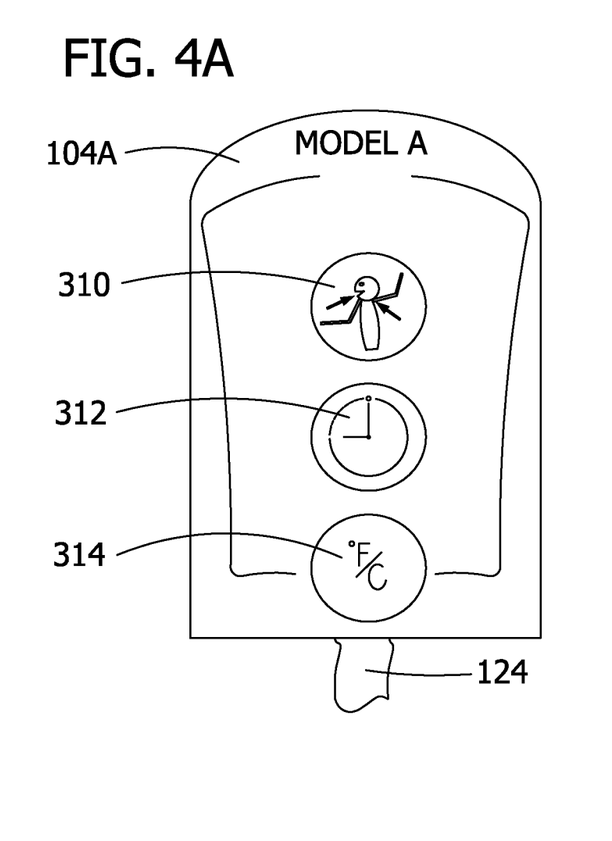
FIGS. 4A, 4B, 4C, and 4D are front views of alternative model selection devices for use in configuring the thermometer of FIG. 2 as different models according to an embodiment of the invention.
Figure 4B:
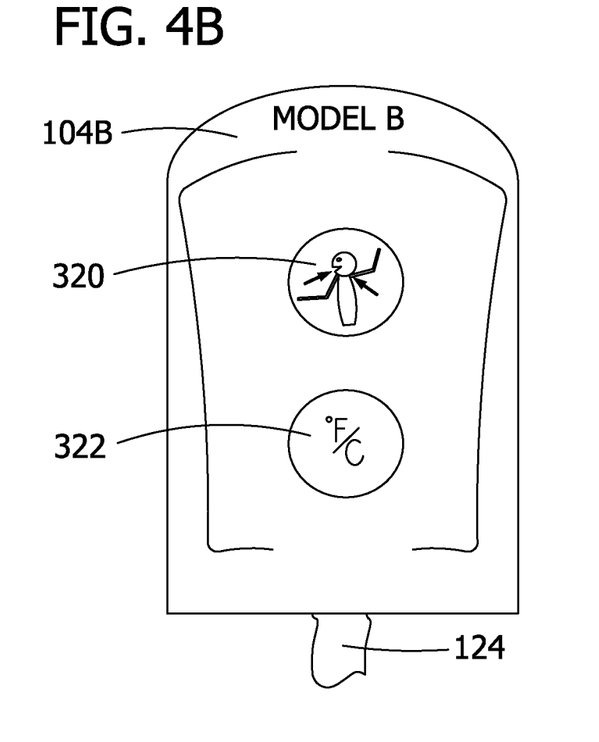
Figure 4C:
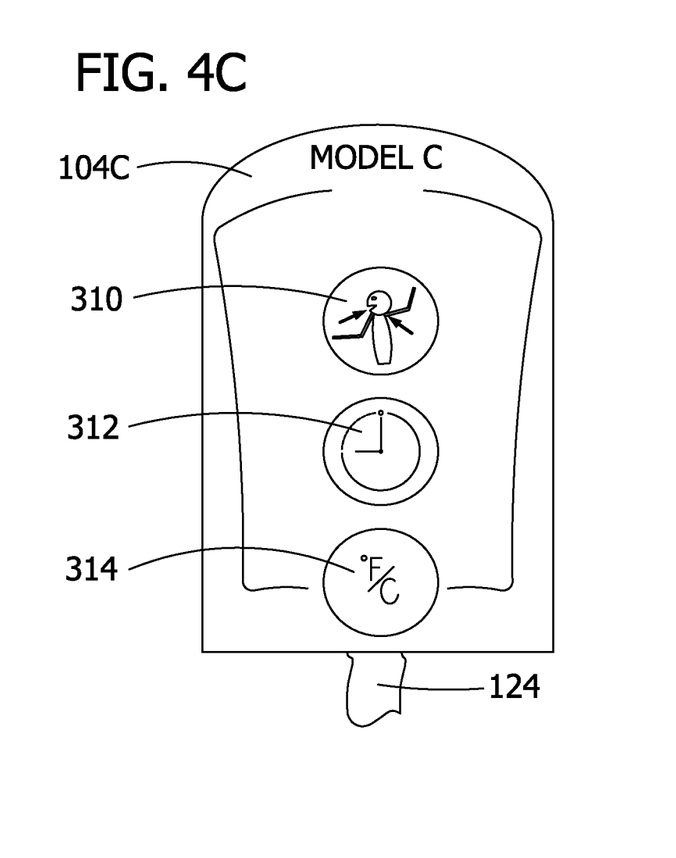
Figure 4D:
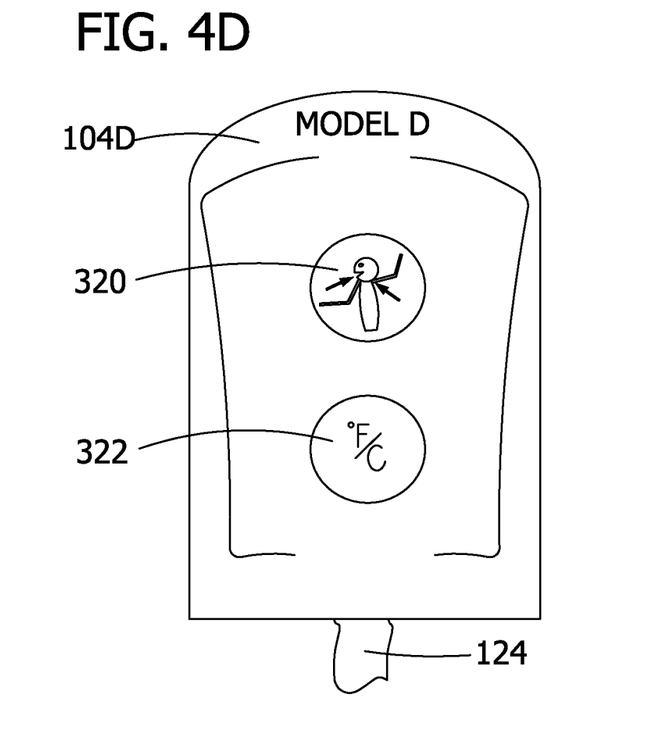

Referring to FIGS. 4A and 4B, two interchangeable user input devices for use with thermometer 100 are shown. For example, a thin laminate overlay includes a circuit sheet having a series of stainless steel domes mounted thereon. The stainless steel domes function as buttons to form a keypad 104A for thermometer 100 and are overlaid with a graphic sheet that includes indicia pertaining to the desired thermometer model. The overlay may also have an adhesive mounting opposite the graphic sheet for mounting to the thermometer housing. During assembly, the overlay keypad 104A is connected to the main circuit board of controller 120 via cable 124 and mating electrical connector (e.g., connector 122). Upon power up, the thermometer software scans the overlay keypad circuitry to determine the type of overlay connected. Based upon the type of overlay keypad sensed, the thermometer software will configure itself to function according to the specifications of the particular model by selectively enabling and/or disabling functions of the thermometer. The software also has instructions for monitoring the sensed keypad periodically during operation of the thermometer for monitoring the thermometer hardware such that if a failure occurs (e.g., keypad 104A is disconnected from the controller 120), the thermometer 100 can display an error on the display 106. It is contemplated that the connector 122 may engage the ribbon cable 124 by any connection method such as a pin header and fitting, an array of spade terminals and fittings, a crimp type fitting, an array of solder joints, or epoxy securing bare ribbon cable wires to corresponding circuit board traces.

In the illustrated embodiment, keypad 104A corresponds to a first thermometer model (e.g., Model A) having a first feature set. A second user input device 104B (i.e., keypad 104B of FIG. 4B) corresponds to a second thermometer model (e.g., Model B) having a second feature set different from the first. It is contemplated that there may be any number of user input devices for use with the thermometer, each user input device corresponding to a different thermometer model having a different feature set, default setting, and/or user interface configuration. The keypad 104A includes three buttons: a measurement site button 310, a timer button 312, and a temperature scale button 314. The measurement site button 310 allows the user to select where to take a patient's body temperature (e.g., select oral or axillary). The timer button 312 allows the user to take a patient's pulse. The t-scale button 314 allows the user to switch the units of the measured temperature shown on the display 106 between Fahrenheit and Celsius. The second keypad 104B includes a temperature site button 320 and a t-scale button 322. The model corresponding to the second keypad 104B does not provide the timer feature. There may be other differences between the first and second feature sets such as a calibration feature and menu, a default units (i.e., Fahrenheit or Celsius) setting, a default site setting, a default predictive mode setting, etc. For example, a full featured model (e.g. Models A and C corresponding to overlays 104A and 104C respectively) provides biotech features (e.g., manual thermometer calibration, direct measurement mode (no prediction algorithms used to speed up measurements), anti-theft settings, preheat temperature, programmable device identification number, sound themes, backlight, measurement counter, LCD display test screens, and battery voltage readout but a less featured model (e.g. Models B and D corresponding to overlays 104B and 104D respectively) does not provide biotech features.

In operation, the keypad 104A or 104B electrically connects at least two pins of the pin header 122 when connected to the pin header 122. It is contemplated that some user input devices do not electrically connect any of the pins and that other user input devices connect multiple pins or sets of pins. When the user turns the thermometer 100 on (e.g., removes the probe, presses a button on the keypad, or activates a power switch of the thermometer 100), the controller 120 determines which pins of the pin header 122 are electrically connected and/or not electrically connected. Based on this determination, the controller 120 sets default parameters of the thermometer 100 and may also selectively enable and/or disable functions and/or menus of the thermometer 100. Thus, the thermometer 100 is configured as the thermometer model, Model A, corresponding to keypad 104A when the keypad 104A is connected, and configured as the thermometer model, Model B, corresponding to the keypad 104B when the keypad 104B is connected.

Figure 5:
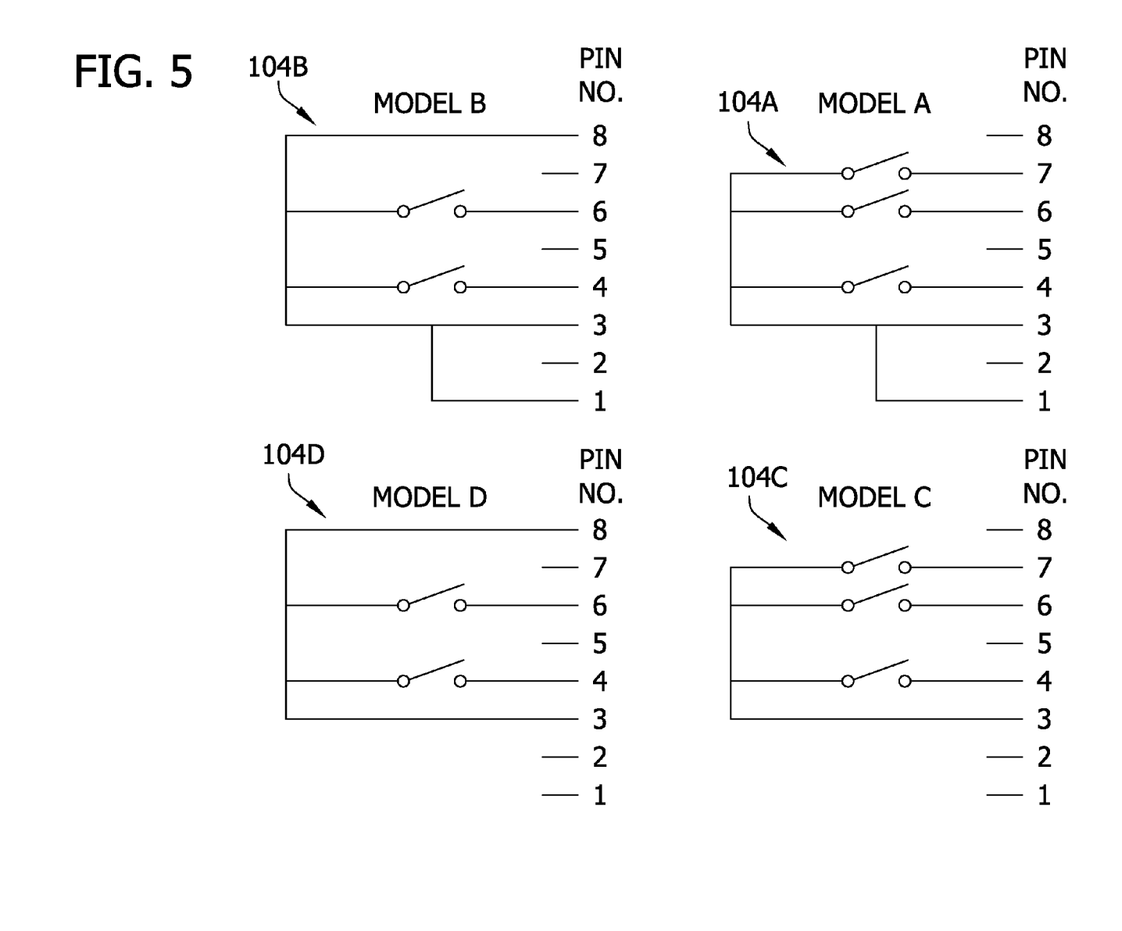
FIG. 5 schematically illustrates exemplary jumper connections of a plurality of model selection devices for configuring the thermometer of FIG. 2 as different models.

Referring to FIG. 5, an exemplary set of connections for the pin header 122 is shown which configure the thermometer 100 as one of a plurality of models (i.e., Models A, B, C, and D). These exemplary connections assume that pin header 122 includes 8 pins. The schematics of Models B and D include a connection between pins 8 and 3 and correspond to the 2 button keypads of FIGS. 4B and 4D. The schematics for Models A and C do not include a connection between pins 8 and 3 and correspond to the 3 button keypads of FIGS. 4A and 4C. Thus, the controller 120 can distinguish Models B and D from Models A and C. Model B includes a connection between pins 1 and 3 whereas Model D does not, and Model A includes a connection between pins 1 and 3 whereas Model C does not. This allows the controller 120 to further distinguish Model B from Model D, and Model A from Model C. Thus, by analyzing which pins of the pin header 122 are connected, the controller 120 can determine the model of a connected keypad and configure the thermometer 100 as the determined model. It is to be understood that other models are available (e.g. by using different pin configurations, decoding schemes, or other component identification schemes).

Figure 6:
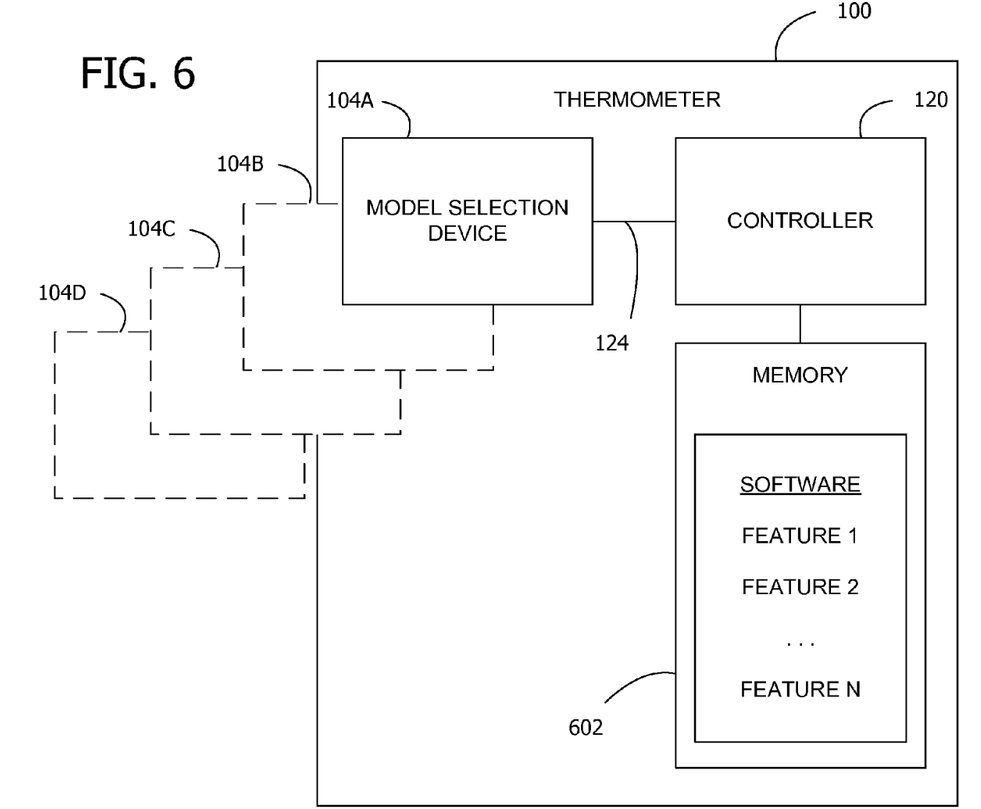
FIG. 6 is a block diagram illustrating the thermometer of FIG. 2 configured according to the embodiment of FIG. 5.

FIG. 6 illustrates thermometer 100 in block diagram form embodying aspects of the invention in accordance with the connections described above with respect to FIG. 5. In FIG. 6, thermometer 100 constitutes a universal electronic thermometer that is automatically configured, upon initialization, as a particular thermometer model, Model A, B, C, or D. The controller 120 of universal thermometer 100 has a memory 602 storing a software program containing instructions for implementing all of the user interface menus and features of which the thermometer is capable. Depending on which of the model selection devices 104A-D are connected to controller 120, controller 120 enables and/or disables features implemented in the software program to cause the thermometer 100 to operate in accordance with the designated model. Having one software program including instructions for all of the features and options of all of the available thermometer models allows a manufacturer to quickly adapt to market needs. For example, the manufacturer or a distributor can stock thermometer cores (i.e., a thermometer with a model selection device not yet installed) and install model selection devices on demand according to a customer order, reconfigure thermometers in inventory as a desired thermometer model by replacing the installed model selection devices, or add features to a customer's existing thermometers by replacing the model selection device.

In an alternative embodiment of the invention, the controller 120 determines the connected model selection device by retrieving, or receiving, an identification code from the model selection device, wherein all of the model selection devices corresponding to a particular thermometer model provide the same identification code. The controller 120 operates the thermometer 100 as a function of the identification code provided by the connected model selection device such that the thermometer 100 is configured as the thermometer model corresponding to the connected model selection device. Transmitting the identification code to the controller 120 may be accomplished via wires, contact, or wirelessly (e.g. via RFID technology). In another embodiment, the controller 120 stores a plurality of software program profiles, and loads a software profile based on the connected model selection device. In yet another embodiment, a touch screen interface is the model selection device and replaces both the user input device and the display and accepts user input and displays the measured patient temperature and menus of the thermometer.

Figure 7:
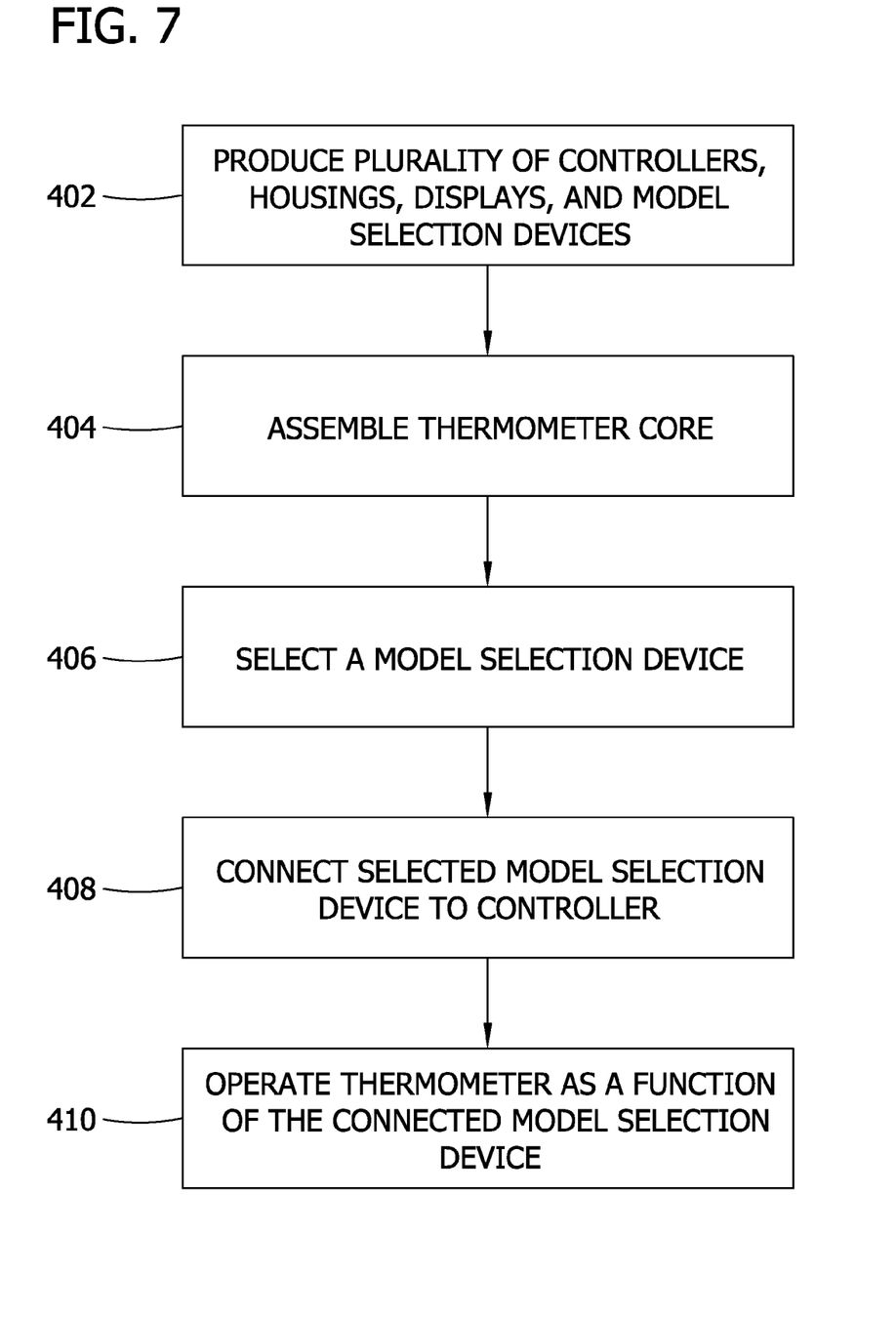
FIG. 7 is an exemplary flow showing aspects of a method of manufacturing a thermometer according to an embodiment of the invention.

Referring to FIG. 7, a method of manufacturing the thermometer 100 is shown. At 402, a manufacturer produces a plurality of controllers, housings, displays, and model selection devices. At 404, the manufacturer assembles the parts (i.e., a controller, a housing, a probe, a cord, a battery, and a display) into a thermometer core (i.e., a thermometer with a model selection device not yet installed). At 406, a model selection device is selected from a plurality of model selection devices. The selected model selection device corresponds to the thermometer model that the manufacturer desires to produce. At 408, the selected model selection device is connected to the controller of the thermometer core to form a completed thermometer (e.g. thermometer 100), and at 410, the controller operates the thermometer as a function of the connected model selection device.

The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

Embodiments of the invention may be implemented with computer-executable instructions. The computer-executable instructions may be organized into one or more computer-executable components or modules. Aspects of the invention may be implemented with any number and organization of such components or modules. For example, aspects of the invention are not limited to the specific computer-executable instructions or the specific components or modules illustrated in the figures and described herein. Other embodiments of the invention may include different computer-executable instructions or components having more or less functionality than illustrated and described herein.

When introducing elements of aspects of the invention or the embodiments thereof, the articles "a," "an," "the," and "said" are intended to mean that there are one or more of the elements. The terms "comprising," "including," and "having"

are intended to be inclusive and mean that there may be additional elements other than the listed elements.

Having described aspects of the invention in detail, it will be apparent that modifications and variations are possible without departing from the scope of aspects of the invention as defined in the appended claims. As various changes could be made in the above constructions, products, and methods without departing from the scope of aspects of the invention, it is intended that all matter contained in the above description and shown in the accompanying drawings shall be interpreted as illustrative and not in a limiting sense.

What is claimed is:

1. A method of configuring a configurable medical device comprising:
    selecting a user input device from a plurality of user input devices for use with the configurable medical device, said configurable medical device having a memory storing a plurality of operating configurations and storing one or more computer-executable instructions for implementing a plurality of functions of the configurable medical device, each of said user input devices being indicative of one of the operating configurations stored in the memory of the configurable medical device;
    connecting the selected user input device to a controller of the configurable medical device; and
    configuring the controller for operating the configurable medical device in a selected operating configuration as a function of the indicative operating configuration of the selected user input device connected to said controller, said configured controller executing software instructions selected from the one or more software instructions to implement one or more of the plurality of functions of the configurable medical device upon said configuring.

2. The method of claim 1 wherein the user input devices comprise a plurality of interchangeable, model-specific keypads, each of said keypads and said controller having mating electrical connectors, and wherein connecting the selected user input device to the controller comprises connecting a selected one of the keypads to the controller via the mating electrical connectors to configure the controller according to the selected operating configuration.

3. The method of claim 1 further comprising storing the computer executable instructions in the memory of the configurable medical device for implementing operation of the plurality of functions of the medical device wherein a subset of said functions defines each of the operating configurations.

4. The method of claim 3 wherein configuring the controller comprises selectively enabling the subset of functions of the medical device based on the selected user input device connected to the controller.

5. The method of claim 3 wherein configuring the controller comprises selectively disabling each of the functions implemented by the computer-executable instructions not in the subset of functions of the medical device based on the selected user input device connected to the controller.

6. The method of claim 1 further comprising storing a plurality of software profiles in the memory of the configurable medical device, said software profiles each being representative of a pre-defined set of medical device functions corresponding to one of the plurality of configurations of the medical device, and wherein configuring the controller comprises loading the software profile corresponding to the selected operating configuration when the medical device initializes.

7. The method of claim 1 wherein configuring the controller comprises determining a default setting of the medical device as a function of the selected user input device connected to said controller.

8. A method of configuring a configurable thermometer comprising:
    selecting a user input device from a plurality of user input devices for use with the configurable thermometer, said configurable thermometer having a memory storing a plurality of operating configurations and storing one or more computer-executable instructions for implementing a plurality of functions of the configurable thermometer, each of said user input devices being indicative of one of the operating configurations stored in the memory of the configurable thermometer;
    connecting the selected user input device to a controller of the configurable thermometer; and
    configuring the controller for operating the configurable thermometer in a selected operating configuration, wherein the configured controller is operable in the selected operating configuration to implement one or more of the plurality of functions of the configurable thermometer as a function of the indicative operating configuration of the selected user input device connected to said controller.

9. The method of claim 8 wherein the user input devices comprise a plurality of interchangeable, model-specific keypads, each of said keypads and said controller having mating electrical connectors, and wherein connecting the selected user input device to the controller comprises connecting a selected one of the keypads to the controller via the mating electrical connectors to customize the configurable thermometer according to the selected operating configuration.

10. The method of claim 8 further comprising storing the computer executable instructions in the memory of the configurable thermometer for implementing operation of the plurality of functions of the configurable thermometer wherein a subset of said functions defines each of the operating configurations.

11. The method of claim 10 wherein configuring the controller comprises selectively enabling the subset of functions of the configurable thermometer based on the selected user input device connected to the controller.

12. The method of claim 8 further comprising storing a plurality of software profiles in the memory of the configurable thermometer, said software profiles each being representative of a pre-defined set of functions corresponding to one of the plurality of operating configurations of the configurable thermometer, and wherein configuring the controller comprises loading the software profile corresponding to the selected operating configuration when the custom thermometer initializes.

13. The method of claim 8 wherein configuring the controller comprises determining a default setting of the configurable thermometer as a function of the selected user input device connected to said controller.

14. A method of configuring a configurable medical device comprising:
    providing a configurable medical device having a memory storing a plurality of operating configurations and storing one or more computer-executable instructions for implementing a plurality of functions of the configurable medical device and having a controller for executing the one or more computer-executable instructions stored in the memory;
    selecting a user input device from a plurality of user input devices for use with the provided configurable medical device, each of said user input devices being indicative of one of the operating configurations stored in the memory of the provided configurable medical device;

connecting the selected user input device to the controller of the provided configurable medical device; and configuring the controller for operating the provided configurable medical device in a selected operating configuration as a function of the indicative operating configuration of the selected user input device connected to said controller, said configured controller selectively executing software instructions selected from the one or more software instructions to implement one or more of the plurality of functions of the provided configurable medical device upon said configuring.

* * * * *